US00PP33458P2

(12) United States Plant Patent
Cherry

(10) Patent No.: US PP33,458 P2
(45) Date of Patent: Sep. 7, 2021

(54) ***CAMELLIA* PLANT NAMED 'CAM130'**

(50) Latin Name: *Camellia sinensis*
Varietal Denomination: CAM130

(71) Applicant: The Paradise Seed Company Pty Ltd., Kariong (AU)

(72) Inventor: Robert Cherry, Gawler (AU)

(73) Assignee: The Paradise Seed Company

( * ) Notice: Subject to any disclaimer, the term of this patent is extended or adjusted under 35 U.S.C. 154(b) by 0 days.

(21) Appl. No.: 17/038,722

(22) Filed: Sep. 30, 2020

(51) Int. Cl.
*A01H 5/02* (2018.01)
*A01H 6/00* (2018.01)

(52) U.S. Cl.
USPC ..... Plt./243
CPC ..... *A01H 6/00* (2018.05)

(58) Field of Classification Search
USPC ..... Plt./243
CPC ..... A01H 5/02; A01H 5/00
See application file for complete search history.

*Primary Examiner* — Kent L Bell
(74) *Attorney, Agent, or Firm* — Cassandra Bright

(57) ABSTRACT

A new and distinct cultivar of *Camellia* plant named 'CAM130' is disclosed, characterized by a distinctive compact, habit. Foliage is dark green and plants have been observed to have good disease resistance. The new cultivar is a *Camellia*, suitable for ornamental garden purposes.

3 Drawing Sheets

Latin name of the genus and species: *Camellia sinensis*.
Variety Denomination: 'CAM130'.

BACKGROUND OF THE INVENTION

The new cultivar is a product of a planned breeding program by the inventor. The open-pollination resulting in the new variety was made August of 1998, at a nursery in Kulnura, Australia. The seed parent is the unpatented proprietary variety *Camellia* 'CamG1'. The pollen parent is unidentified. The inventor discovered this new variety at the same nursery in August of 2002.

After identifying the new variety as a potentially interesting selection, the inventor first propagated plants of 'CAM130' by semi-hardwood vegetative cuttings during January of 2005 at the same commercial nursery in Kulnura, Australia. The inventor continued confidential, controlled testing and propagation (via semi-hardwood cuttings), assessing stability of the unique characteristics of this variety. Multiple generations have been reproduced and have shown that the unique features of this cultivar are stable and reproduced true to type.

SUMMARY OF THE INVENTION

The cultivar 'CAM130' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'CAM130'. These characteristics in combination distinguish 'CAM130' as a new and distinct *Camellia* cultivar:

1. Compact habit.
2. Dark green foliage.
3. Good disease resistance.

COMPARISON TO PARENT VARIETY

'CAM130' is similar in most horticultural characteristics to the seed parent variety *Camellia* 'Buttons'. Plants of the new cultivar 'CAM130' however, differ in the following:

1. The new variety has darker green leaves (near Yellow-Green 147A) compared to the seed parent (near Yellow-Green 146A).
2. 'Cam130' has a different leaf cross section (flat—slightly concave) compared to seed parent (concave).
3. Plants of the new variety are more compact than plants of the seed parent.

COMMERCIAL COMPARISON

'CAM130' can be compared to the commercial variety *Camellia* 'Yabukita', unpatented. Plants of the new cultivar 'CAM130' are similar to plants of 'Yabukita' in most horticultural characteristics, however, plants of the new cultivar 'CAM130' differ in the following:

1. 'Cam130' has a shorter leaf blade (75-80 mm) than 'Yabukita' (95-110 mm).
2. 'Cam130' has a more narrow leaf blade (av. 30 mm) than 'Yabukita' (av. 40 mm).
3. 'Cam130' has shorter laterals (av. 30 cm) than 'Yabukita' (av. 50 cm).

BRIEF DESCRIPTION OF THE PHOTOGRAPHS

The accompanying photograph in FIG. 1 illustrates in full color a plant of 'CAM130' grown outdoors in Kulnura, Australia.

Figure 1:
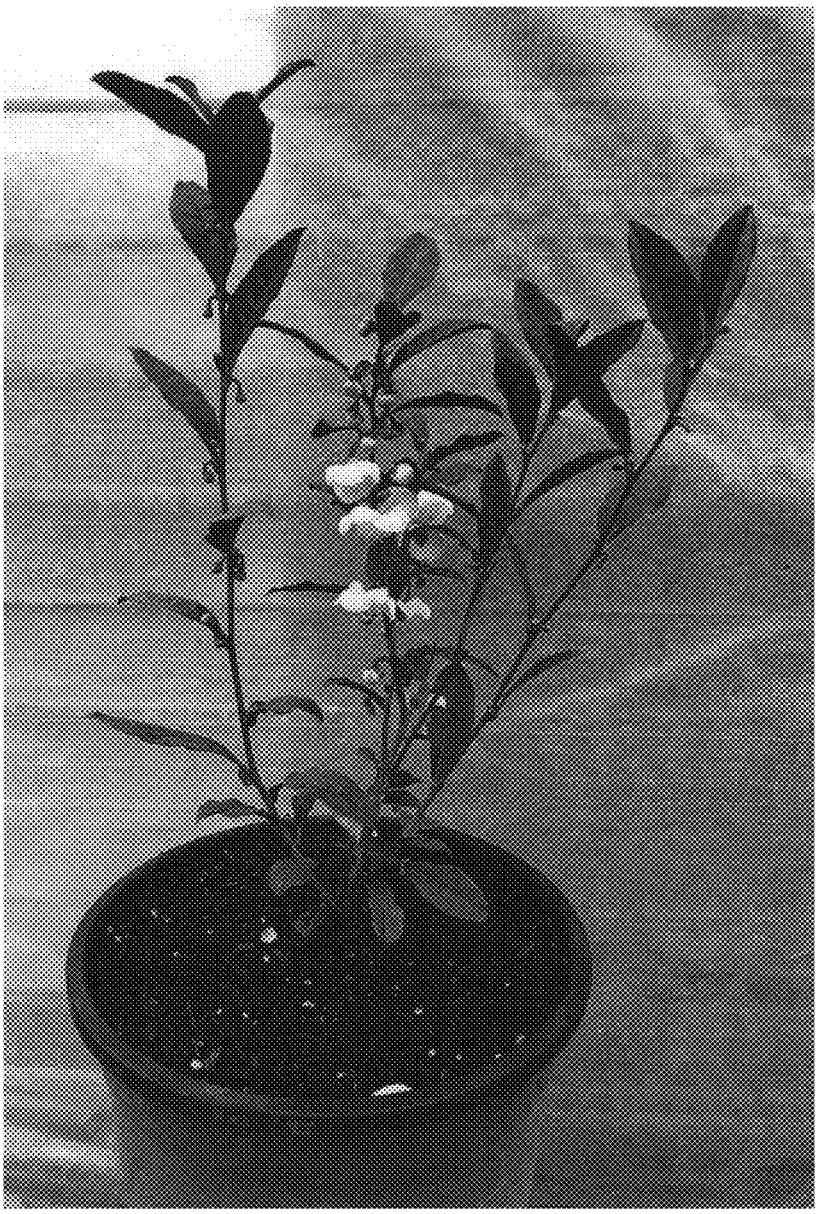
Figure 2:
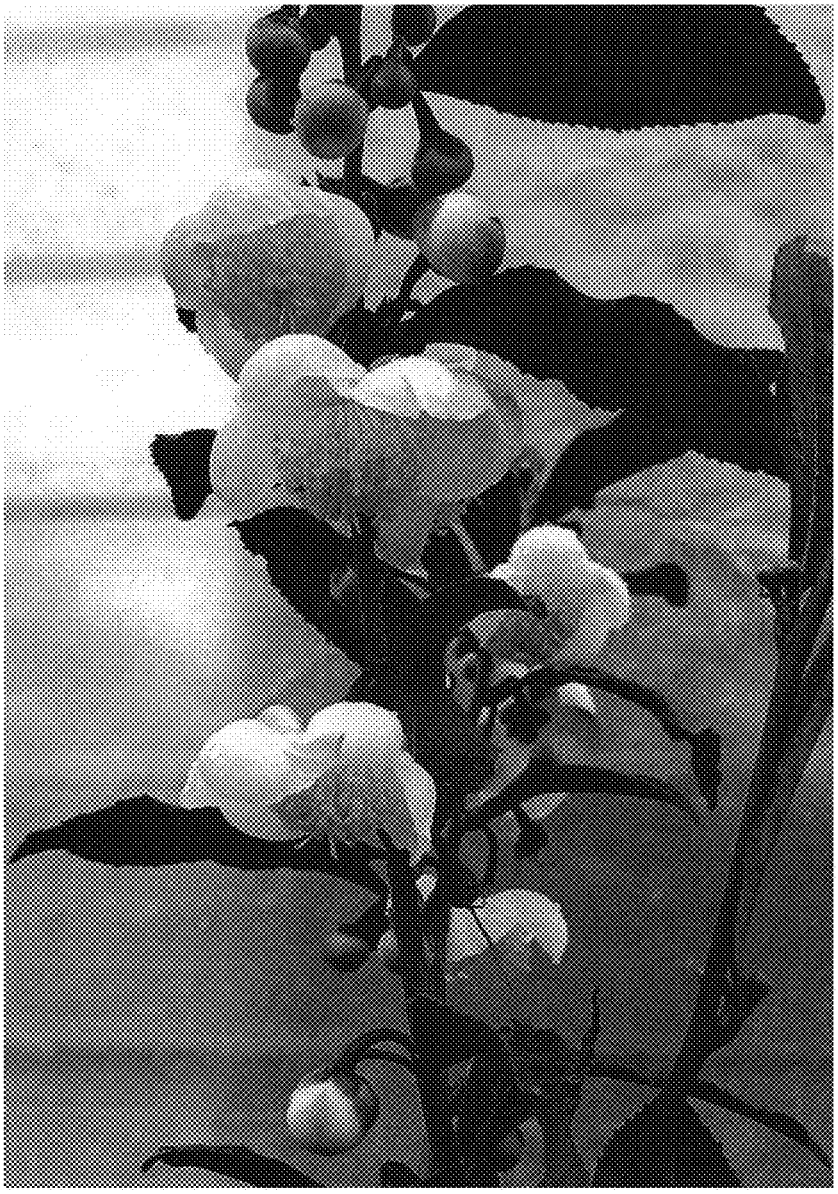
FIG. 2 shows a closer view of flowers on plants of the new variety.
Figure 3:
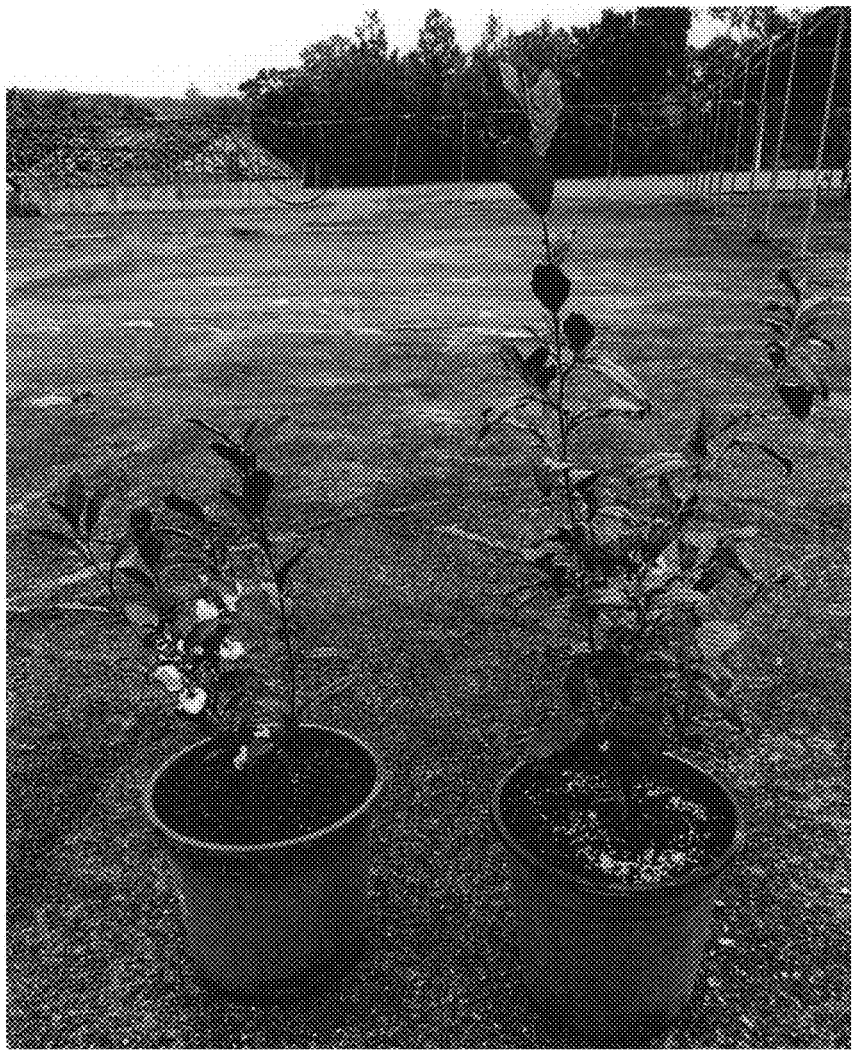
FIG. 3 is a comparison with the variety 'YABUKITA'. 'Cam130' is the smaller plant on the left side of the photos, 'YABUKITA' is the taller plant on the right. Plants photographed are approximately 12 months old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'CAM130' plants grown outdoors in the Summer, in Kulnura, Australia. Plants are approximately 12 months old, in 250 mm pots. The average day time temperature is around 22° C., average night temperature is around 13° C. Plants were grown under 30% shade cloth in a pine bark based potting media. Measurements and numerical values represent averages of typical plant types.

Botanical classification: *Camellia sinensis* 'CAM130'.

PROPAGATION

Typically by semi-hardwood cuttings in Spring and Summer.

Time to Rooting: 28-70 days at approximately 25° C.

Time to produce a rooted young plant: About 4 months.

Root description: Fleshy, new roots colored RHS White 155D.

PLANT

Growth habit: Upright, compact evergreen flowering shrub.

Shape: V-shaped.

Height: 50 cm.

Plant spread: 30 cm.

Vigor: Moderate.

Branching characteristics:

- *Length*.—30 cm.
- *Diameter*.—2-3 mm.
- *Strength*.—Strong.
- *Texture*.—Slightly rough.
- *Color*.—Mature branches: Near RHS Greyed-Orange 165A. Young branches: Near RHS Green 143C.
- *Internode*.—About 5 cm.

FOLIAGE

Leaf:

- *Type*.—Simple.
- *Arrangement*.—Alternate.
- *Average length*.—75 to 80 mm.
- *Average width*.—30 mm.
- *Shape of blade*.—Elliptic.
- *Apex*.—Acuminate.
- *Base*.—Attenuate.
- *Attachment*.—Petiolate.
- *Margin*.—Serrulate.
- *Aspect*.—Flat to slightly concave.
- *Texture of top surface*.—Glabrous.
- *Texture of bottom surface*.—Glabrous.
- *Appearance of top surface*.—Medium glossy.
- *Appearance of bottom surface*.—Matte.
- *Color*.—Young foliage upper side: Near RHS Green 137A. Young foliage under side: Near RHS Green 137D. Mature foliage upper side: Near RHS Yellow-Green 147A. Mature foliage under side: Near RHS Yellow-Green 147B.
- *Venation*.—Type: Pinnate. Venation color upper side: Near RHS Yellow-Green 147B. Venation color under side: Near RHS Yellow-Green 147B Petiole:

- *Length*.—5 to 8 mm.
- *Diameter*.—2 mm.
- *Texture*.—Glabrous.
- *Color*.—Near RHS Yellow-Green 147B.

FLOWER

Bloom period: Summer to Autumn.

Peduncle:

- *Length*.—Average 20 mm.
- *Diameter*.—Average 3-4 mm.
- *Color*.—Near RHS Yellow-Green 147A.
- *Texture*.—Smooth.
- *Aspect*.—Downward facing.
- *Strength*.—Strong.

Flowers:

- *Arrangement*.—Single rotate axillary. 1 to 2 per axil is most common up to 5 per axil occur.
- *Shape*.—Shallowly cup shaped.
- *Facing direction*.—Pedicellate, nodding.
- *Quantity of flowers per lateral stem*.—Up to 30.
- *Quantity of flowers and buds per plant*.—Approximately 100 to 120.
- *Diameter of entire flower*.—Approximately 3 cm to 5 cm.
- *Depth/length of flower*.—Approximately 2 cm.
- *Rate of opening*.—Individual flowers: Fully open approximately 5-7 days from the bud stage. Whole Plant: Approximately 50% of flowers open at once.
- *Flower longevity on plant*.—Approximately 5 days.
- *Persistent or self-cleaning*.—Self-cleaning.
- *Fragrance*.—Light.

Petals:

- *Length of petal*.—Approximately 2 cm.
- *Width of petal*.—Approximately 2 cm.
- *Apex*.—Obtuse/rounded.
- *Shape of petal*.—Broad oval to sub-orbicular.
- *Petal margin*.—Entire, concave.
- *Petal arrangement*.—Slightly overlapping.
- *Petal number*.—5-7.
- *Petals fused*.—No.
- *Petal appearance*.—Slightly translucent.
- *Petal texture*.—Smooth, delicate, both upper and lower surfaces.

Color:

- *Upper surface at first opening*.—Near RHS White NN155B.
- *Upper surface at maturity*.—Near RHS White NN155B.
- *Upper surface at fading*.—Near RHS White NN155B.
- *Under surface at first opening*.—Near RHS Green-White 157D.
- *Under surface at maturity*.—Near RHS White NN155B.
- *Under surface at fading*.—Near RHS White NN155B.

Petaloids: Absent.

Bud:

*Shape*.—Orbicular.

*Length*.—About 1 cm.

*Diameter*.—About 1 cm.

*Color*.—Near RHS Yellow-Green 150D, base near 147B.

*Texture*.—Glabrous.

Sepal:

*Number*.—5.

*Sepal arrangement*.—Whorled.

*Sepal length*.—Approximately 2-3 mm.

*Sepal width*.—Approximately 2-3 mm.

*Sepal shape*.—Broadly ovate.

*Base*.—Obtuse.

*Apex shape*.—Obtuse.

*Margin*.—Entire.

*Color*.—Near RHS Yellow-Green 147A, both upper and lower surfaces.

*Texture*.—Glabrous, both upper and lower surfaces.

REPRODUCTIVE ORGANS

Stamens:

*Number*.—Average range 150 to 200.

*Length*.—Approximately 10 mm.

*Width*.—Approximately 1 mm.

*Anthers*.—Length: Approximately 1 mm. Width: Approximately 1 mm. Color: Near RHS Yellow-Orange 14A. Pollen Quantity and Color: Abundant. RHS Yellow-Orange 14A. Shape: Linear.

Pistil:

*Number*.—1.

*Length*.—Approximately 15 mm.

*Style*.—Length: Approximately 10 mm. Color: Near RHS Yellow-Green 150D. Stigma Shape and Color: Forked, near RHS Yellow-Green 150D. Ovary Shape, Size, Color: Orbicular. Approximately 5 mm in length, 5 mm in diameter, color near RHS Yellow-Green 150D.

OTHER CHARACTERISTICS

Disease and pest resistance: Good resistance to *Camellia* related leaf diseases such as *Pestalotiopsis*. Neither resistance nor susceptibility to normal pests of *Camellia* observed.

Temperature tolerance: Cold tolerance to Zone 7. Heat tolerance to at least 35° C.

Fruit/seed production: approx 3-4 seed per capsule, brown (near RHS N200), rounded approx 1 cm in diameter.

What is claimed is:

1. A new and distinct cultivar of *Camellia* plant named 'CAM130' as herein illustrated and described.

* * * * *